United States Patent [19]
van der Hagen

[11] Patent Number: 6,147,040
[45] Date of Patent: Nov. 14, 2000

[54] TRANSPATENT TOILET BAR CONTAINING A DECORATIVE CONCENTRIC PATTERN

[75] Inventor: John van der Hagen, Leander, Tex.

[73] Assignee: Surrey, Inc., Leander, Tex.

[21] Appl. No.: 09/374,755

[22] Filed: Aug. 13, 1999

[51] Int. Cl.$^7$ .................................................. A61K 7/50
[52] U.S. Cl. ........................ 510/146; 510/147; 510/152; 510/155; 510/156
[58] Field of Search ................... 510/141, 146, 510/147, 152, 155, 156

[56] References Cited

U.S. PATENT DOCUMENTS

| | | | |
|---|---|---|---|
| 4,634,564 | 1/1987 | Kerslake | 264/75 |
| 4,851,147 | 7/1989 | Esposito et al. | 252/108 |
| 4,963,284 | 10/1990 | Novakovic et al. | 252/108 |
| 5,703,025 | 12/1997 | Zyngier et al. | 510/147 |
| 5,786,311 | 7/1998 | Zyngier et al. | 510/147 |

*Primary Examiner*—Necholus Ogden
*Attorney, Agent, or Firm*—Rick B. Yeager

[57] ABSTRACT

A transparent toilet bar with an embedded decorative concentric pattern comprised of colored transparent soap formulations, and a method for producing the bar. The preferred embodiment of the bar is a transparent semi-circular rainbow pattern of three or more colors embedded in a transparent rectangular bar with a glittering agent. The preferred method of producing the rainbow is to pour a first color into a small circular mold and then to place that circular soap article into a larger mold and pour a second color around the soap article. A third concentric ring is created by repeating the process with a larger third mold. The finished disk is cut in half to create two rainbow soap articles. In the preferred embodiment of the method, all soap compositions are identical except for color or glitter additives.

9 Claims, 3 Drawing Sheets

TRANSPATENT TOILET BAR CONTAINING A DECORATIVE CONCENTRIC PATTERN

FIELD OF INVENTION

The present invention relates to a decorative article of soap and a process for making that article.

BACKGROUND

The present invention relates to a process for the preparation of soap articles containing a decorative concentric colored pattern in a clear or colored transparent soap.

Transparent soaps are popular with consumers, and many consumers desire decorative soap articles comprised of transparent soap formulations.

The prior art includes numerous formulations and process for transparent and translucent soaps. U.S. Pat. No. 4,584,126 issued to Joshi on Apr. 22, 1986 provides a background on formulations and manufacturing processes for translucent and transparent soaps.

The prior art also includes transparent soaps with embedded soap shapes, printed films, and other articles. U.S. Pat. No. 5,217,639 issued Jun. 8, 1993 to Mottola describes a dual-phase toilet bar having a first portion that is at least translucent and a second portion that is opaque. A process is disclosed wherein a clear composition is poured to partly fill a mold. Thereafter, an opaque composition is poured into the remaining volume of the mold, this composition being essentially identical to the clear composition but also including a small amount of solid particulate opacifying agent. Alternatively, the opaque composition may be poured first into the mold followed by the clear composition.

An object of the present invention is to provide a transparent soap bar having a decorative internal layer without requiring different soap formulations other than color additives.

U.S. Pat. No. 4,504,433 issued Mar. 12, 1985 to Inui et al describes a process for the preparation of soap articles containing dried shapes also formed of soap. The process comprises the steps of placing a dried shape of colored soap on a supporting base of transparent soap which has been cooled to solidification but not been dried; and then adding transparent soap, which may or may not be colored; cooling to solidification; and removing the solidified transparent soap, followed by drying the soap.

It is an object of the present invention to provide a unique and aesthetically pleasing transparent toilet bar incorporating a decorative concentric colored pattern.

A still further object of the present invention is to provide a process for manufacturing a transparent toilet bar incorporating a decorative concentric colored pattern.

These and other objects of the present invention will become more apparent from the summary, detailed description and example which follow.

SUMMARY OF THE INVENTION

The current invention is a toilet bar comprising a decorative concentric pattern comprised of colored transparent soap, and a method for producing the bar.

The preferred embodiment of the bar is a transparent rainbow pattern of three or more colors embedded in a transparent rectangular bar with a glittering agent.

The preferred method of producing the bar is to produce a rainbow and to insert the rainbow into a mold which forms the transparent rectangular bar. The rainbow is produced by pouring the first transparent colored soap composition into a first round mold; cooling the first composition to form a first round colored transparent bar; placing the first colored transparent bar into a second, larger, round mold; pouring a second transparent colored soap composition into the second round mold; cooling the second mold contents to form a bar having a concentric pattern of the first and second transparent colors; placing the cooled bar into a third, larger, round mold; pouring a third transparent colored soap composition into the third round mold; cooling the third mold contents to form a bar having a concentric pattern of the first, second, and third transparent colors; removing the bar and cutting it in half, thereby creating two rainbow soap articles.

In the preferred embodiment of the method, a three color rainbow is embedded in a transparent rectangular bar.

BRIEF DESCRIPTION OF THE DRAWINGS

The above-mentioned and other objects and features of the present invention will become apparent from a reading of the following detailed description with reference to the accompanying drawings, in which.

DETAILED DESCRIPTION THE PREFERRED EMBODIMENT

The term "transparent" as used in this specification is intended to connote its usual dictionary definition. A transparent soap allows ready viewing of objects behind it; while a translucent soap will allow light to pass through in a scattered manner that makes difficult to clearly identify objects behind the translucent soap. A practical test for transparency is to place a ¼ inch thick section of the soap article over a printed matter having a bold-faced type of 14 point size. If the print can easily be read, then the bar is considered to be transparent. In the preferred embodiment, transparency or optical clarity is achieved independent of color of the bar.

Figure 1:
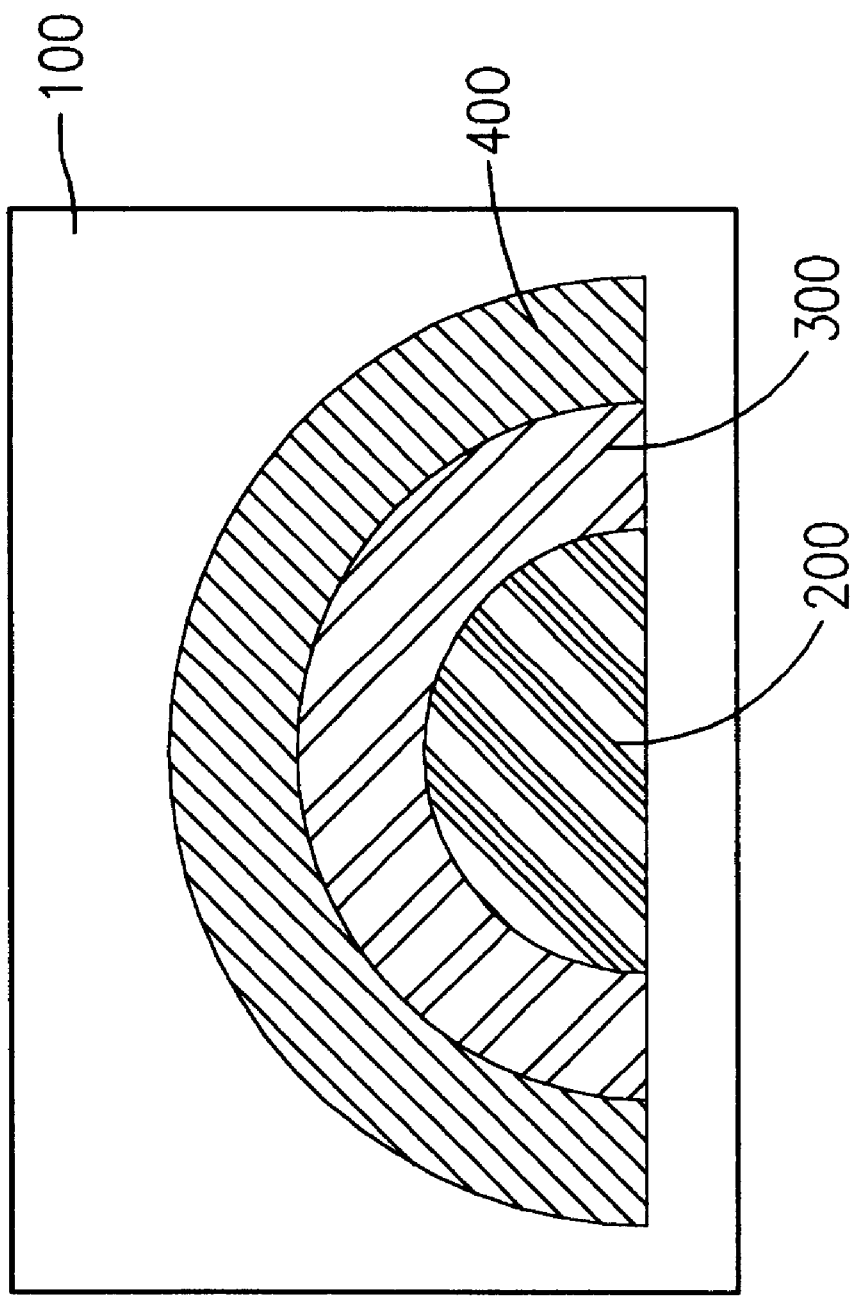
FIG. 1 is a top view of a finished bar showing a colored rainbow embedded soap article.

Referring now to FIG. 1, the finished bar consists of a three-color rainbow, which is made from sequential pours of various colors of transparent soap 200, 300, and 400, embedded in a rectanglar transparent bar 100.

The preferred embodiment of the invention utilizes a clear transparent soap base of the following approximate composition. All parts, percentages and proportions referred to herein and in the appended claims are by weight unless otherwise indicated:

| | |
|---|---|
| Propylene Glycol | 22% |
| Sorbitol 70% | 13 |
| Sodium Lauryl Ether Sulfate | 10.5 |
| Stearic Acid | 12 |
| Myristic Acid | 5 |
| Glycerine | 12 |
| Water | 11.5 |
| NaOH (50% with Water) | 5 |
| TEA (Triethanolamine) | 1 |

| | |
|---|---|
| Sodium Cocoyl Isethionate | 7 |
| Fragrance | 1 |
| Color | |

Color is preferably obtained by the addition of a 1% solution of FD&C Red #40, Red #4, Yellow #5, D&C Red #33, or other Food, Drug, and Cosmetic or Drug & Cosmetic colors in 50% propylene glycol and deionized water. Each of the soap compositions in the rainbow and in the rectangular bar are based on this preferred composition with the addition of a colored dye mixture.

The transparent soap formulation is prepared in a 1000 pound batch by mixing the Propylene Glycol, Sorbitol 70%, and Sodium Lauryl Ether Sulfate at a temperature in the range of 155–170° F., preferably at 160° F.; and then continuing to add the Stearic Acid, Myristic Acid, Glycerine, and water while maintaining the temperature at 160° F.; adding the 50% NaOH solution, which will cause the temperature to rise approximately 10 to 15° F.; and then continuing to add the remaining ingredients. The final temperature will typically be in the range of 155 to 160° F.

Figure 3:
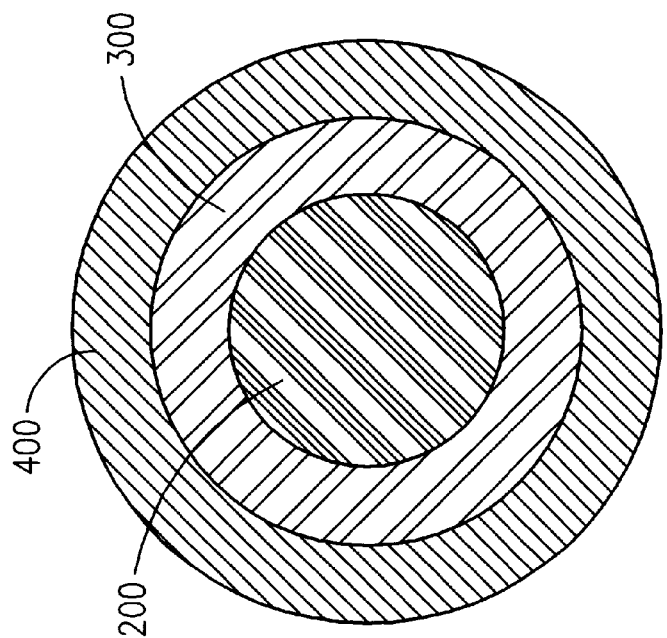
FIG. 3 is a top view illustrating the sequential formation of concentric colored soap rings.
Figure 3:
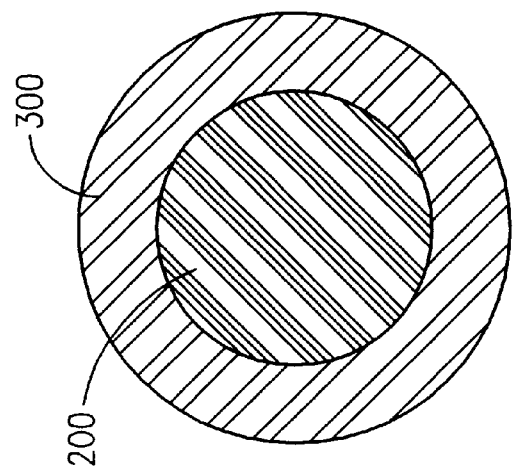
Figure 3:
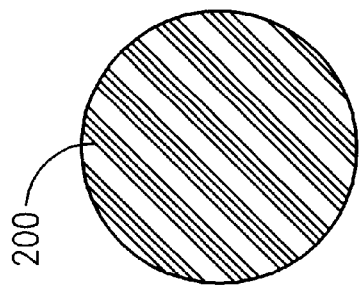

Referring now to FIG. 3, the rainbow colored decoration is formed by pouring a first yellow colored transparent soap composition 200 into a circular mold having a diameter of about 1 inches and a depth of about ½ inch. After cooling, the yellow disk is removed from the mold and placed in a second mold having a diameter of approximately 2 inches and a depth of about ½ inch. This second larger mold is filled with a red colored transparent soap composition 300. After cooling, the yellow and red disk is removed from the mold and placed in a third mold having a diameter of approximately 3 inches and a depth of about ½ inch. This third larger mold is filled with a green colored transparent soap composition 400. The yellow, red, and green soap compositions are preapred by adding the respective dye mixture to the base transparent soap composition. It is generally desirable to use diluted dye mixtures to minimize excessive color bleed and transfer of color from the soap bar to the hands of the user, and to create a light colored pattern in the finished article.

Once the temperature has cooled to approximately room temperature, the yellow, red and green soap disk is cut in half, thereby forming two semi-circular rainbow soap articles. Each rainbow is then placed to form the decorative colored layer of the preferred embodiment of the current invention.

Figure 2:
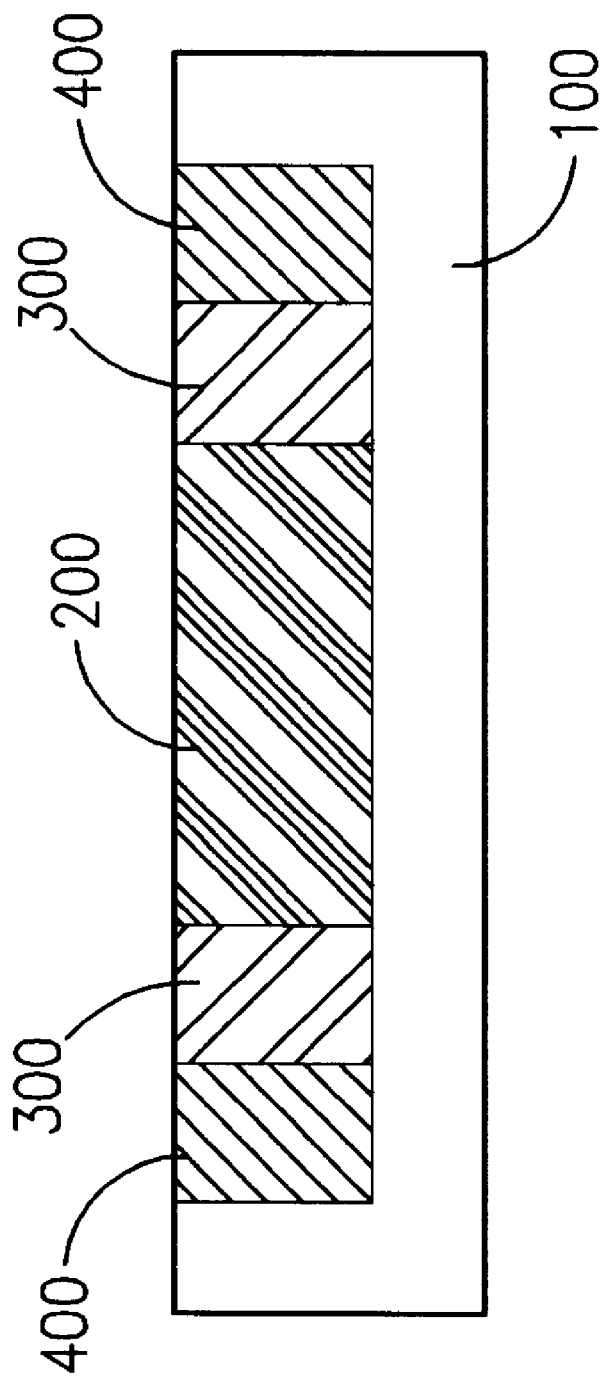
FIG. 2 is a cross section of a finished bar showing a colored rainbow embedded soap article.

Referring now to FIG. 2, the preferred method of manufacture of the decorative article is to place the embedded concentric decorative soap article in a silicone mold and to pour a molten transparent soap mixture 100 into the mold so that the transparent soap mixture surrounds and embeds the concentric decorative soap article. Typically, a six-cavity silicone release mold will be used for a standard size bar of soap. These release molds are commercially available. Each cavity is in the shape of the finished article of soap.

The manufacture is typically performed on a conveyor production line. As the partially filled molds move down the line, cooling takes place and the bars begin to solidify. The cooling is typically enhanced in a coolant chamber maintained at approximately 34° F. The partially filled mold is cooled until the soap composition reaches a temperature of approximately 77 to 82° F., which typically requires approximately 30 minutes of cooling.

The full soap cavity molds are cooled on the production line, removed from the mold and wrapped or packaged for sale. The preferable composition for manufacture is a clear transparent soap composition.

The effect of this manufacturing process is to produce a soap article having an embedded concentric colored layer of decoration. Optionally, a relatively small amount of glitter may be added to the formulation for additional decorative effect.

The shape of the concentric article is not limited to a semi-circular rainbow pattern Article, and concentric patterns including ovals, rectangles, polygons, and, circular, or other shapes may be used. The shape of the finished soap bar is not limited to a rectangle, and ovals, circles, polygons, and other shapes may be used.

In alternative embodiments, the clear transparent composition may be replaced by another color or may include decorative elements such as a glitter additive.

Various modifications of the formula and process will be apparent to one skilled in the art.

ALTERNATE EMBODIMENT—PACKAGING MOLDS

In alternative embodiments, the finished article may be prepared directly in blister packages or clamshell packages rather than silicone molds.

What is claimed is:

1. A toilet bar comprising:
   a rainbow soap pattern comprised of at least three concentric semicircular rings of colored transparent soap; and
   a transparent soap formulation is comprised of about 22% by weight propylene glycol; 13% by weight of 70% sorbitol; 10.5% by weight sodium lauryl ether sulfate; 12% by weight stearic acid; 5% by weight myristic acid; 12% by weight glycerine; 11.5% by weight water; 5% by weight of a 50% sodium hydroxide and water solution; 1% by weight triethanolamine; 7% by weight sodium cocoyl isethionate; and 1% fragrance solution, such that the rainbow soap pattern is embedded in the transparent soap formulation, such that the rainbow soap pattern may be viewed from the top of the toilet bar.

2. The toilet bar of claim 1 wherein
   a glitter is included in the transparent soap formulation.

3. The toilet bar of claim 1 wherein
   a glitter is included in at least one of the rings of the colored transparent soap.

4. The toilet bar of claim 1 wherein
   the toilet bar is rectangular in shape.

5. The toilet bar of claim 4 wherein
   the toilet bar is approximately two inches wide, three inches long, and ¾ inches thick.

6. The toilet bar of claim 4 wherein
   the upper surface of the toilet bar is convex.

7. The toilet bar of claim 1 wherein
   the thickness of the rainbow soap pattern is 30 to 70% of the thickness of toilet bar.

8. The toilet bar of claim 1 wherein
   the length of the rainbow soap pattern is 80 to 99% of the length of the toilet bar.

9. The toilet bar of claim 1 wherein
   the thickness of the rainbow soap pattern is 30 to 70% of the thickness of toilet bar.

* * * * *